United States Patent
Rasmussen et al.

(10) Patent No.: US 8,569,029 B2
(45) Date of Patent: *Oct. 29, 2013

(54) DNASE EXPRESSION IN RECOMBINANT HOST CELLS

(75) Inventors: Michael Dolberg Rasmussen, Vallensbaek (DK); Jon Martin Persson, Bjaerred (SE)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/532,268

(22) Filed: Jun. 25, 2012

(65) Prior Publication Data

US 2012/0264169 A1  Oct. 18, 2012

Related U.S. Application Data

(63) Continuation of application No. 12/516,720, filed as application No. PCT/EP2007/063109 on Nov. 30, 2007, now Pat. No. 8,227,227.

(60) Provisional application No. 60/870,156, filed on Dec. 15, 2006.

(30) Foreign Application Priority Data

Nov. 30, 2006  (DK) .................................. 2006 01581

(51) Int. Cl.
  *C12N 9/00*  (2006.01)
  *C12N 1/20*  (2006.01)
(52) U.S. Cl.
  USPC ...................................... 435/183; 435/252.31
(58) Field of Classification Search
  None
  See application file for complete search history.

(56) References Cited

U.S. PATENT DOCUMENTS

| 6,083,718 A | 7/2000 | Sanders |
| 2002/0110860 A1 | 8/2002 | Bron |

FOREIGN PATENT DOCUMENTS

| WO | 03/054140 A2 | 7/2003 |

OTHER PUBLICATIONS

Nakamura et al. Eur. J. Biochem. (1992) 209, 121-127.*
Kovacevic et al. J. Bacteriol. (1985) 162 (2), 521-528.*
Allenby et al, Microbiology 150, 2619-2628 (2004).
Boynton et al, Appl Env Microbiol 65(4), 1524-1529 (1999).
Cooke et al, J Biotechnol 101, 229-239 (2003).
Haidinger et al, Appl Environ Microbiol 69(10), 6106-6113 (2003).
Hoi et al, Proteomics 6, 3582-3601 (2006).
Kerovuo et al, Biotechnol Letters 22, 1311-1317 (2000).
Miller et al, J Bacteriol 169(8), 3508-3415 (1987).
Miyoshi et al, FEMS Microbiol Letters 239, 205-212 (2004).

* cited by examiner

*Primary Examiner* — Nashaat Nashed
(74) *Attorney, Agent, or Firm* — Eric J. Fechter

(57) ABSTRACT

The present invention relates to cells producing at least one polypeptide of interest and expressing one or more recombinant nuclease encoding gene(s) thereby producing the nuclease(s), and methods for producing a polypeptide of interest essentially free from contaminating DNA, said method comprising the steps of:

(a) cultivating a cell that produces at least one polypeptide of interest and expresses one or more recombinant nuclease encoding gene(s) thereby producing the nuclease(s); and
(b) isolating the polypeptide of interest.

20 Claims, 11 Drawing Sheets

Figure 4 (continued on next page)
| Time relative to onset of PO4-starvation/ Fermentation time (BPN100) | A). FACS analysis | B). Phase contrast microscopy | C). Fluorescence microscopy |
|---|---|---|---|
| -4 hours/ 27.6 h | 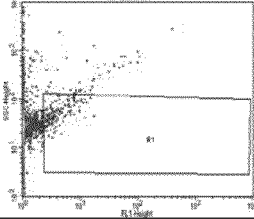 | No picture | No picture |
| -3 hours/ 28.6 h | 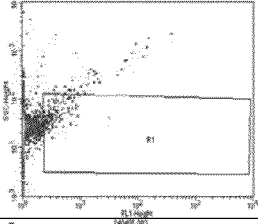 | No picture | No picture |
| -2 hours/ 29.6 h | 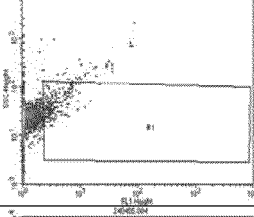 | No picture | No picture |
| -1 hour/ 30.6 h | 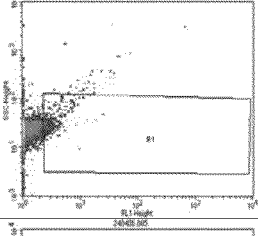 | No picture | 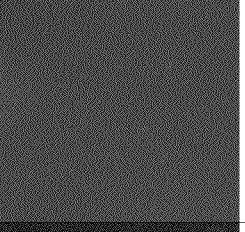 |
| 0 hours/ 31.6 h | 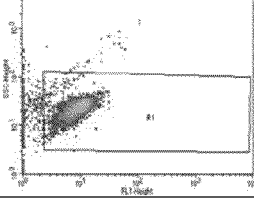 | 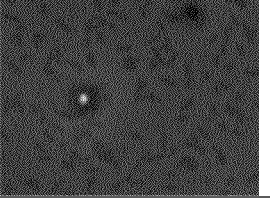 | 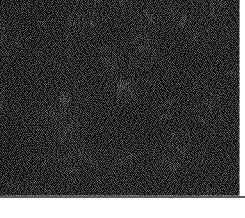 |

Figure 9

5 min incub.

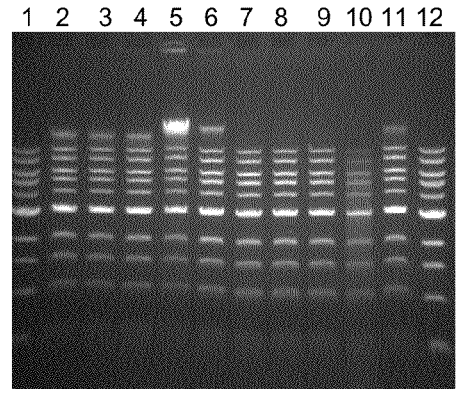

30 min incub.

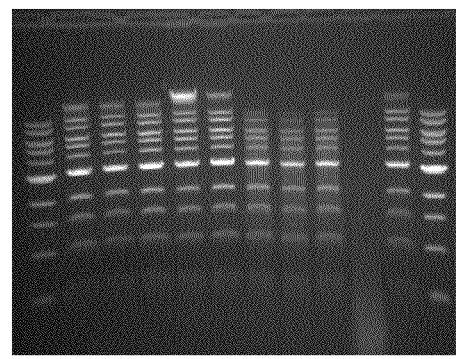

120 min incub.

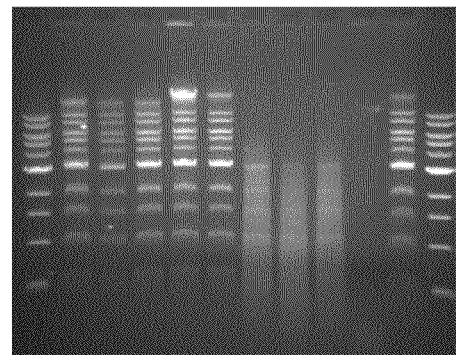

Lane 1: Marker DNA
Lane 2: Marker DNA + MOL2716 strain (+ phosphate)
Lane 3: Marker DNA + MOL2717 strain (+ phosphate)
Lane 4: Marker DNA + MOL2718 strain (+ phosphate)
Lane 5: Marker DNA + MOL2684 strain (+ phosphate)
Lane 6: Marker DNA + Sm-30 strain (+ phosphate)
Lane 7: Marker DNA + MOL2716 strain (- phosphate)
Lane 8: Marker DNA + MOL2717 strain (- phosphate)
Lane 9: Marker DNA + MOL2718 strain (- phosphate)
Lane 10: Marker DNA + MOL2684 strain (- phosphate)
Lane 11: Marker DNA + Sm-30 strain (- phosphate)
Lane 12: Marker DNA

Figure 10

5 min incub.

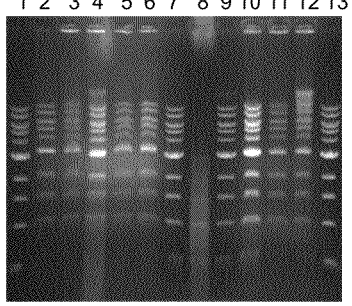

60 min incub.

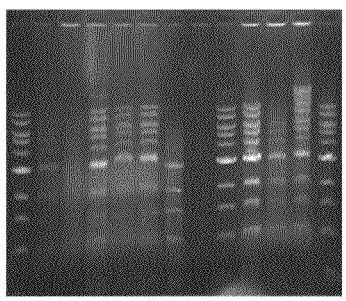

240 min. incub

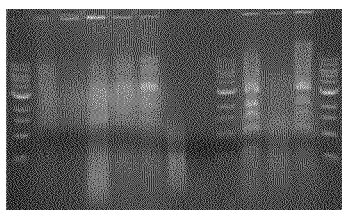

Lane 1:  Marker DNA
Lane 2:  Marker DNA + MOL2717 strain, 1 liter fermentation (- phosphate), 1. day
Lane 3:  Marker DNA + MOL2717 strain, 1 liter fermentation (- phosphate), 2. day
Lane 4:  Marker DNA + MOL2717 strain, 1 liter fermentation (- phosphate), 3. day
Lane 5:  Marker DNA + MOL2717 strain, 1 liter fermentation (- phosphate), 4. day
Lane 6:  Marker DNA + MOL2717 strain, 1 liter fermentation (- phosphate), 5. day
Lane 7:  Marker DNA + MOL2717 strain, TY medium (- phosphate), overnight
Lane 8:  Marker DNA + MOL2684 strain, TY medium (- phosphate), overnight
Lane 9:  Marker DNA + Sm-30 strain, TY medium (- phosphate), overnight
Lane 10: Marker DNA + MOL2717 strain, PS1 medium, 7 days
Lane 11: Marker DNA + MOL2684 strain, PS1 medium, 7 days
Lane 12: Marker DNA + Sm-30 strain, PS1 medium, 7 days
Lane 13: Marker DNA

SEQUENCE LISTING

<160> NUMBER OF SEQ ID NOS: 12

<210> SEQ ID NO 1
<211> LENGTH: 7765
<212> TYPE: DNA
<213> ORGANISM: Artificial sequence
<220> FEATURE:
<223> OTHER INFORMATION: Plasmid pAN238

<400> SEQUENCE: 1

```
cgagctcatt attaatctgt tcagcaatcg ggcgcgattg ctgaataaaa gatacgagag      60
acctctcttg tatctttttt attttgagtg gttttgtccg ttacactaga aaaccgaaag     120
acaataaaaa ttttattctt gctgagtctg gctttcggta agctagacaa aacggacaaa     180
ataaaaattg gcaagggttt aaaggtggag atttttttgag tgatcttctc aaaaaatact     240
acctgtccct tgctgatttt taaacgagca cgagagcaaa acccccttt gctgaggtgg      300 cagagggcag gttttttttgt ttcttttttc tcgtaaaaaa aagaaaggtc ttaaaggttt     360
tatggttttg gtcggcactg ccgacagcct cgcagagcac acactttatg aatataaagt     420
atagtgtgtt atactttact tggaagtggt tgccggaaag agcgaaaatg cctcacattt     480
gtgccaccta aaaaggagcg atttacatat gagttatgca gtttgtagaa tgcaaaaagt     540
gaaatcagct ggactaaaag gcagagctcg gtacccgggg atcctctaga gtcgattatg     600
```

-continued

```
tcttttgcgc agtcggctta aaccagtttt cgctggtgcg aaaaaagagt gtcttgtgac      660
acctaaattc aaaatctatc ggtcagattt ataccgattt gattttatat attcttgaat      720
aacatacgcc gagttatcac ataaaagcgg gaaccaatca tcaaatttaa acttcattgc      780
ataatccatt aaactcttaa attctacgat tccttgttca tcaataaact caatcatttc      840
tttaattaat ttatatctat ctgttgttgt tttctttaat aattcatcaa catctacacc      900
gccataaact atcatatctt cttttgata tttaaattta ttaggatcgt ccatgtgaag       960
catatatctc acaagacctt tcacacttcc tgcaatctgc ggaatagtcg cattcaattc     1020
ttctgtaatt attttatct gttcataaga tttattaccc tcatacatca ctagaatatg      1080
ataatgctct ttttcatcc taccttctgt atcagtatcc ctatcatgta atggagacac      1140
tacaaattga atgtgtaact cttttaaata ctctaaccac tcggcttttg ctgattctgg     1200
atataaaaca aatgtccaat tacgtcctct tgaattttc ttgttttcag tttcttttat      1260
tacattttcg ctcatgatat aataacggtg ctaatacact taacaaaatt tagtcataga    1320
taggcagcat gccagtgctg tctatctttt tttgtttaaa atgcaccgta ttcctccttt     1380
gcatattttt ttattagaat accggttgca tctgatttgc taatattata ttttctttg     1440 attctattta atatctcatt ttcttctgtt gtaagtctta aagtaacagc aacttttttc     1500
tcttcttttc tatctacaac catcactgta cctcccaaca tctgtttttt tcactttaac    1560
ataaaaaaca accttttaac attaaaaacc caatatttat ttatttgttt ggacaatgga    1620
caatggacac ctaggggga ggtcgtagta ccccccctatg ttttctcccc taaataaccc    1680 caaaatcta agaaaaaaag acctcaaaaa ggtctttaat taacatctca aatttcgcat     1740
ttattccaat ttccttttg cgtgtgatgc gctgcgtcca ttaaaaatcc tagagctttg     1800
aaaccgaaag ttaatagctg tcgctactac tttcgcttac gctctaagta tattttaagg    1860
actgtcacac gcaaaaagtt ttctcggcat aaaagtacct ctacatctct aaatcgtctg    1920
tacgctgttt ctcacgcttt ctatcgacct tctggacatt atcctgtaca acatccataa    1980
actgtcccac acgctcaaat ttggaatcat taaagaattt ctctttaagc ctattaaacc    2040 cttttctcaaa cccagggaaa ttcgccctcg cagcacgata taaagtcact gtactagctt    2100
gaaatttctc tgatacattc aactgctcat tcaaactatc attctctcgc tttaatttat    2160
taacctcttt acttttttcg tgatacccct ctttccatgt attcactact tctttcaaac    2220
tctctctacg ttttttttaat tcttgatttt ctgtgtaata gtctgtgctc ttaatatttt    2280
cgtaatcatc aacaatccgt tctgcagaag agattgtttc ttgcaggcgt tcaaattcat    2340
cagcagttaa tatcttttcta ccagtctctt cacgtccaga gaacaaacct gtacgctcat    2400
tttcataatc aaagggtttc gtagacctca tatgctctat tccactctgt aactgcttat    2460
ttgccttctg taactcatcc ttaacttctt gcagttcctg tttatgaaat acagtatctt    2520
tcttgtactg atccatcgct ttatgttctc gttctgtaac ctctttggac gtgcctcttt    2580
caagttcata acctttctca ttcacatact cattaaatct atcttgtaat tgagtaaagt    2640
ctttcttgtt gcctaactgt tctttttgcag acaatctccc gtcctctgtt aaagggacaa    2700
aaccaaagtg catatgtggg actctttcat ccagatggac agtcgcatac agcatatttt    2760
ccttaccgta ttcattttct agaaactcca agctatcttt aaaaaatcgt tctatttctt    2820
ctccgcttaa atcatcaaag aaatcttat cacttgtaac cagtccgtcc acatgtcgaa     2880
ttgcatctga ccgaattta cgtttccctg aataattctc atcaatcgtt tcatcaattt     2940
tatctttata cttatattt tgtgcgttaa tcaaatcata attttttatat gtttcctcat    3000
```

```
gatttatgtc tttattatta tagtttttat tctctctttg attatgtctt tgtatcccgt    3060
ttgtattact tgatccttta actctggcaa ccctcaaaat tgaatgagac atgctacacc    3120
tccggataat aaatatatat aaacgtatat agatttcata aagtctaaca cactagactt    3180
atttacttcg taattaagtc gttaaaccgt gtgctctacg accaaaacta taaaacctttt   3240 aagaactttc ttttttttaca agaaaaaaga aattagataa atctctcata tcttttattc   3300
aataatcgca tccgattgca gtataaattt aacgatcact catcatgttc atatttatca    3360
gagctcgtgc tataattata ctaatttttat aaggaggaaa aaatatgggc atttttagta   3420
tttttgtaat cagcacagtt cattatcaac caaacaaaaa ataagtggtt ataatgaatc    3480
gttaataagc aaaattcata taccaaatt aaagagggtt ataatgaacg agaaaaatat     3540
aaaacacagt caaaacttta ttacttcaaa acataatata gataaaataa tgacaaatat    3600
aagattaaat gaacatgata atatctttga aatcggctca ggaaaaggcc attttaccct    3660
tgaattagta aagaggtgta atttcgtaac tgccattgaa atagaccata aattatgcaa    3720
aactacagaa aataaacttg ttgatcacga taatttccaa gttttaaaca aggatatatt    3780
gcagtttaaa tttcctaaaa accaatccta taaaatatat ggtaatatac cttataacat    3840
aagtacggat ataatacgca aaattgtttt tgatagtata gctaatgaga tttatttaat    3900
cgtggaatac gggtttgcta aaagattatt aaatacaaaa cgctcattgg cattacttttt  3960 aatggcagaa gttgatattt ctatattaag tatggttcca agagaatatt ttcatcctaa    4020
acctaaagtg aatagctcac ttatcagatt aagtagaaaa aaatcaagaa tatcacacaa    4080
agataaacaa aagtataatt atttcgttat gaaatgggtt aacaaagaat acaagaaaat    4140
atttacaaaa aatcaatttta acaattcctt aaaacatgca ggaattgacg atttaaacaa    4200
tattagcttt gaacaattct tatctcttttt caatagctat aaattattta ataagtaagt    4260
taagggatgc atttcgttgt ccaccaagcc gggcacgcac acgccgattc cggtcaatcc    4320
gaatggggaa ggcggtatttt tgtcaacggc aagccccgtc aattcgatta atgcctcttc    4380
tgtcgcctga atgtcttctt catcaagcgt tcgttcgaat tgttcaatca aatgcccttc    4440
aaggtcggtt aacgcaacaa ttatataatt ggttccgaca tctacaccga ccgcatagcc    4500
ggcttttcga ttgaatttca gcataacggg ccttctgccg ccgcttgact cgccggggcc    4560
ggtttcataa atgatgtcct tttgaagcag ggaagacact tgggaggaaa cggtcgcttt    4620
atttaatcct gttatttccg aaagtttggc ccttgagacg ggtccgtttt caataatctg    4680
ctcaaaaatc agggctttgt tcattttttt tacaagggct tgatccgctg tattcaatgt    4740
caatcactcc attgctttga agctgtgaat ttattatagt ataacaaatt tgaaaacttt     4800 atttttttcct ctatttccat tgaaagcgat taattgatcc tgtaaaatac atacaaggaa   4860
gttagtttaa tggttaaaca acattgtttt tttaacgtttt gcaaggaaaa gtgaaggggg   4920
agatcggaat gttttttaga aatatcgaaa tgattgagta tgaaggggcc gattaggtaa    4980
tcgatcgtcg acgcgttaaa aatgaggagg gaagctttat gagtaaagga gaagaacttt    5040
tcactggagt tgtcccaatt cttgttgaat tagatggcga tgttaatggg caaaaattct    5100
ctgttagtgg agagggtgaa ggtgatgcaa catacggaaa acttaccctt aaatttattt    5160
gcactactgg gaagctacct gttccatggc caacgcttgt cactactctc tcttatggtg    5220
ttcaatgctt ttctagatac ccagatcata tgaaacagca tgactttttc aagagtgcca    5280
tgcccgaagg ttatgtacag gaaagaacta tattttacaa agatgacggg aactacaaga    5340
cacgtgctga agtcaagttt gaaggtgata cccttgttaa tagaatcgag ttaaaaggta    5400
```

```
ttgattttaa agaagatgga aacattcttg gacacaaaat ggaatacaat tataactcac    5460
ataatgtata catcatggca gacaaaccaa agaatggcat caaagttaac ttcaaaatta    5520
gacacaacat taaagatgga agcgttcaat tagcagacca ttatcaacaa aatactccaa    5580
ttggcgatgg ccctgtcctt ttaccagaca accattacct gtccacgcaa tctgcccttt    5640
ccaaagatcc caacgaaaag agagatcaca tgatccttct tgagtttgta acagctgctg    5700
ggattacaca tggcatggat gaactataca aataaatgtc cagacttcca attgacacta    5760
aagggatcca gaagcggcaa cacgctaatc aataaaaaaa cgctgtgcgg ttaaagggca    5820
cagcgttttt ttgtgtatga atcgaaaaag agaacagatc gcaggtctca aaaatcgagc    5880
gtaaagggct gatccgcggc cgcgaaggaa ccgccctttg cagcataggc acctcggggg    5940
ttgttctcac atatgaatca aaccgtgatc aagagtttaa tggcaatatt cattttctga    6000
accatgcagc ccccgatgcg ttttattcga tgggagtgac gctttctgca ggacgcagct    6060
tcagctggtt taaagatgta tttgccgggc aggcgtcatt tgacgaatta atcagcgata    6120
ttggccattc ccgtcccggg gccgggggac tgctgtttac cccttacttg tcagggagaa    6180
gaactcctca tgccgacgca gatattgcgc ccagcttcat cgggatggac agcgcacata    6240
cacgggcgga ctttgtcaga gccgttattg aaggcattac attctcccct catgaaagca    6300
ttgaacaatt ccgtgccggg ggaaaagaca tcagccgtgt gatttcaatc ggaggaggcg    6360
ccaaaagcaa tcaatggctg caaatccagg cggatatctt caacgccgac atcatcagac    6420
tgacaagcga acaggggccg gcatacggtg cagccatgat cgcggccgtc gggtgcggct    6480
ggtttccgtc gcttgaggct tgtgcagacc ccgcggagat ctgagtaaac attttagagt    6540
gattatcctc aattttctaa gttcttttat aggtattact gcttattgaa cgcgcagacg    6600
gaaggtagtg agcgtgaaac gctgttccat attactagct acattataaa aatttaatga    6660
atattattcc ggtcagcata attagaatcc caacaatttg ccaaatttga atgccatatt    6720
tacttgagcg ccaccaacca aattgttgaa ccaacatact gcctaaaatt tgtccaatca    6780
agcccatcat aattgtcagc cctgcaccaa tttgcggaac agcaacgact gttgcaaaaa    6840
cgattgaggc tcctaaaaat ccaccaattc cattccaagg ttttgctttt tttaattctg    6900
aaatttttgg caaacggcgg tcaataaaaa gagacacgat aaaaatagct aaaaatccaa    6960
tgaagaacga aacaaaggtt gcttgtgcag tgttttcaag taaaactccc aatctgccat    7020
taattgcttg ttgagcagcc gacattgccc caacgatgac cgcccaaatt cgccagccta    7080
gtaagttagt ttggtgcgtt tctgcttctt tttcttttaa attaggaaga acaaccgcga    7140
caataacccc agctaaagta atgataactc ccaaaaagcg catcagagtc atcggaagtt    7200
gcatggcatg aaaccagcca atgaatcaa taagtgtccc catcaatatt cgacccaaaa    7260
taggtaaaat caccgtttgg acagctccta atcttgggaa aagtaaaaca ttagatgtta    7320
gaaaatcccc accaagaacc ccaccaatcc atatccatac tgggtgtgag ccaacaaatt    7380
gaaaactagg aaaaagtgtt tgactggtca ctaaagtgat aattcctaaa aaatcgaac    7440 caacaaagtt ggaaattcca gaggccaaaa atggtgagcc aacaattttt cgtaaatccg    7500
cattgattgg attttgatta gcaagtaaaa aaccgccaac taatgcaaaa gctaggtaaa    7560
tatacattgt ttctccttta aataagtgtt tttacagctt ttataaaagc tgggatttt    7620 ttaatgctac cacattttg tgattttag atagggtttc tcttagaata actcaagtta    7680
ttttttgaga tagtctttca tttcttcaaa agtcacttca ttaattttag cggtgccaat    7740
ttcaggaaca ataaggatct gaatt                                          7765
```

<210> SEQ ID NO 2
<211> LENGTH: 39
<212> TYPE: DNA
<213> ORGANISM: Artificial sequence
<220> FEATURE:
<223> OTHER INFORMATION: Primer 480596

<400> SEQUENCE: 2
tttattatcg atcaagagga ggttgttttt gtcatgatc                                39

<210> SEQ ID NO 3
<211> LENGTH: 36
<212> TYPE: DNA
<213> ORGANISM: Artificial sequence
<220> FEATURE:
<223> OTHER INFORMATION: Primer 480597

<400> SEQUENCE: 3
tttattacgc gtatccccca caacgatttt cctgtc                                   36

<210> SEQ ID NO 4
<211> LENGTH: 43
<212> TYPE: DNA
<213> ORGANISM: Artificial sequence
<220> FEATURE:
<223> OTHER INFORMATION: Primer 480598

<400> SEQUENCE: 4
ttatttatcg ataaggtatg gggggatggg gatgaaaaaa tgg                           43

<210> SEQ ID NO 5
<211> LENGTH: 37
<212> TYPE: DNA
<213> ORGANISM: Artificial sequence
<220> FEATURE:
<223> OTHER INFORMATION: Primer 480599

<400> SEQUENCE: 5
ttatttacgc gtcagctcgg cgaaggattg taacaac                                  37

<210> SEQ ID NO 6
<211> LENGTH: 5863
<212> TYPE: DNA
<213> ORGANISM: Artificial sequence
<220> FEATURE:
<223> OTHER INFORMATION: Plasmid pAN167

<400> SEQUENCE: 6
ccgcggtcgg tacctcaagc ttgaacgcgt gatctagacc agttccctga gcttccgtca         60
gtcggatccc attgcggaaa atagtcatag gcatcctgga attcaatgtt gcgaataatg        120
acgttatcac tcttgatttg gaagtttcct cccacgactt tagcgttagt ccctgaaccg        180
acgatcgtcg tgtttgcagg gatatccacc atgacccgtg ctttttggtt tttctgagag        240
cgtgctctcg cttcttcttg tgttcccgac ggctcttttt tgccccatgt gctaggatca        300
taggctttca aatatttgtc caaatcatac tccggatctt tatagtcatt taggccaagc        360
ggcttcagat tgtcatccac gttcatgtca atcgttccct tgatataaat gattttggc         420 gttgtgttcc tttccttccc taatgccgag acaagctggt ttctgttgct gacggtatac        480
acatttgagg aggatgcttt tgatccgcct gtcgtgccgg tcgagtacgc gccccagcca        540
tcattggatc ccaacgtctg gtggcctaaa tcagctgcgt tcgcgccagc tggagtcaat        600
cctaaaaaca aagccgtagc taacatcaaa agggcctcgt gatacgccta ttttatagg        660

```
ttaatgtcat gataataatg gtttcttaga cgtcaggtgg cacttttcgg ggaaatgtgc    720
gcggaacccc tatttgttta tttttctaaa tacattcaaa tatgtatccg ctcatgagac    780 ataaccctg ataaatgctt caataatatt gaaaaaggaa gagtatgagt attcaacatt    840
tccgtgtcgc ccttattccc ttttttgcgg cattttgcct tcctgttttt gctcacccag    900
aaacgctggt gaaagtaaaa gatgctgaag atcagttggg tgcacgagtg ggttacatcg    960
aactggatct caacagcggt aagatccttg agagttttcg ccccgaagaa cgttttccaa   1020
tgatgagcac ttttaaagtt ctgctatgtg gcgcggtatt atcccgtgtt gacgccgggc   1080
aagagcaact cggtcgccgc atacactatt ctcagaatga cttggttgag tactcaccag   1140
tcacagaaaa gcatcttacg gatggcatga cagtaagaga attatgcagt gctgccataa   1200
ccatgagtga taacactgcg gccaacttac ttctgacaac gatcggagga ccgaaggagc   1260
taaccgcttt tttgcacaac atgggggatc atgtaactcg ccttgatcgt tgggaaccgg   1320
agctgaatga agccatacca aacgacgagc gtgacaccac gatgcctgca gcaatggcaa   1380
caacgttgcg caaactatta actggcgaac tacttactct agcttcccgg caacaattaa   1440
tagactggat ggaggcggat aaagttgcag gaccacttct gcgctcggcc cttccggctg   1500
gctggtttat tgctgataaa tctggagccg gtgagcgtgg gtctcgcggt atcattgcag   1560
cactggggcc agatggtaag ccctcccgta tcgtagttat ctacacgacg gggagtcagg   1620
caactatgga tgaacgaaat agacagatcg ctgagatagg tgcctcactg attaagcatt   1680
ggtaactgtc agaccaagtt tactcatata ctttagat tgatttaaaa cttcattttt   1740
aatttaaaag gatctaggtg aagatccttt ttgataatct catgaccaaa atcccttaac   1800
gtgagttttc gttccactga gcgtcagacc ccgtagaaaa gatcaaagga tcttcttgag   1860 atccttttt tctgcgcgta atctgctgct tgcaaacaaa aaaaccaccg ctaccagcgg   1920
tggtttgttt gccggatcaa gagctaccaa ctctttttcc gaaggtaact ggcttcagca   1980
gagcgcagat accaaatact gtccttctag tgtagccgta gttaggccac cacttcaaga   2040
actctgtagc accgcctaca tacctcgctc tgctaatcct gttaccagtg gctgctgcca   2100
gtggcgataa gtcgtgtctt accgggttgg actcaagacg atagttaccg gataaggcgc   2160
agcggtcggg ctgaacgggg ggttcgtgca cacagcccag cttggagcga acgacctaca   2220
ccgaactgag atacctacag cgtgagctat gagaaagcgc cacgcttccc gaagggagaa   2280
aggcggacag gtatccggta agcggcaggg tcggaacagg agagcgcacg agggagcttc   2340 caggggaaa cgcctggtat ctttatagtc ctgtcgggtt tcgccacctc tgacttgagc   2400
gtcgattttt gtgatgctcg tcagggggc ggagcctatg gaaaaacgcc agcaacgcgg   2460
cccgacctcg agctggatac ttccgtccg ccaggggac atgccggcga tgctgaaggt   2520
cgcgcgcatt cccgatgaag aggcggtta ccgcctgttt gaggatatag taatcttct   2580 aaatagcttt ggattggagg agtatgggga gatcaggaa tgagtttata aaataaaaaa   2640
agcacctgaa aagtgtctt ttttgatgg ttttgaactt gttctttctt atcttgatac   2700
atatagaaat aacgtcattt ttatttagt tgctgaaagg tgcgttgaag tgttggtatg   2760
tatgtgtttt aaagtattga aaaccctaa aattggttgc acagaaaac cccatctgtt   2820 aaagttataa gtgactaaac aaataactaa atagatgggg gtttctttta atattatgtg   2880
tcctaatagt agcatttatt cagatgaaaa atcaagggtt ttagtggaca agacaaaaag   2940
tggaaaagtg agaccatgat gcttaggaag acgagttatt aatagctgaa taagaacggt   3000
gctctccaaa tattcttatt tagaaaagca aatctaaaat tatctgaaaa gggaatgaga   3060
```

```
atagtgaatg gaccaataat aatgactaga gaagaaagaa tgaagattgt tcatgaaatt    3120
aaggaacgaa tattggataa atatggggat gatgttaagg ctattggtgt ttatggctct    3180
cttggtcgtc agactgatgg gccctattcg gatattgaga tgatgtgtgt catgtcaaca    3240
gaggaagcag agttcagcca tgaatggaca accggtgagt ggaaggtgga agtgaatttt    3300
gatagcgaag agattctact agattatgca tctcaggtgg aatcagattg gccgcttaca    3360
catggtcaat tttctctat tttgccgatt tatgattcag gtggatactt agagaaagtg     3420
tatcaaactg ctaaatcggt agaagcccaa acgttccacg atgcgatttg tgcccttatc    3480
gtagaagagc tgtttgaata tgcaggcaaa tggcgtaata ttcgtgtgca aggaccgaca    3540
acatttctac catccttgac tgtacaggta gcaatggcag gtgccatgtt gattggtctg    3600
catcatcgca tctgttatac gacgagcgct tcggtcttaa ctgaagcagt taagcaatca    3660
gatcttcctt caggttatga ccatctgtgc cagttcgtaa tgtctggtca actttccgac    3720
tctgagaaac ttctggaatc gctagagaat ttctggaatg ggattcagga gtggacagaa    3780
cgacacggat atatagtgga tgtgtcaaaa cgcataccat tttgaacgat gacctctaat    3840
aattgttaat catgttggtt acgtatttat taacttctcc tagtattagt aattatcagc    3900
ggccccacta atactaagtt cagctaataa aaaaatttgc taaagaactc cagctggatt    3960
tcactgatga gaatatcgtc ggagataaat ataataattc cacggactat agactatact    4020
agtatactcc gtctactgta cgatacactt ccgctcaggt ccttgtcctt taacgaggat    4080
tgttaccgac taagaaaatg ccgtcaaatc cgctcgccat gacttcacgt cgacccgcac    4140
ccgcttgatt tataacattt gatttcacat tagcagaagc atcaatcgat ccatgcagag    4200
acggcgtcca gccgacagaa gagctcagcc cgtttcagc cgatgcgttg atctgtgtgc     4260
cgttcagcaa cgtgccggag tcatataaag ccgttccccc gctgaatacg ctgatcgttt    4320
tagcagctga cagtcccggt acgtcaatga cattgttttg ggcatagatt ttagatgact    4380
ttccgattcc ccatgcatag ctaaaaggat aacttgaaga gcttgtgctt ccttcataat    4440
agttgttgta tacgtgcact tgcccgaagc ggactctcgg cgcgcgctgg acaatatttt    4500
tatagcggtt atgatgcagc gtaattttta atttgccgtc atcggaggtt ttgctgtcac    4560
ttgatccgaa aatggagctt ttatcatgat cgtgataata gttgtaggac atcgtgtatat   4620
agttagcacc gttggaagca tccgtttggc cgtcatggtg ctgatatttt cttccataat    4680
atttcggtga tgtgctgtcc ggacgcgaac cgtgtcggcg atataggcgc cagcaaccgc    4740
acctgtggcg ccggtgatgc cggccacgat gcgtccggcg tagaggatct ggagctgtaa    4800
tataaaaacc ttcttcaact aacggggcag gttagtgaca ttagaaaacc gactgtaaaa    4860
agtacagtcg gcattatctc atattataaa agccagtcat taggcctatc tgacaattcc    4920
tgaatagagt tcataaacaa tcctgcatga taaccatcac aaacagaatg atgtacctgt    4980
aaagatagcg gtaaatatat tgaattacct ttattaatga attttcctgc tgtaataatg    5040
ggtagaaggt aattactatt attattgata tttaagttaa acccagtaaa tgaagtccat    5100
ggaataatag aaagagaaaa agcattttca ggtataggtg ttttgggaaa caatttcccc    5160
gaaccattat atttctctac atcagaaagg tataaatcat aaaactcttt gaagtcattc    5220
tttacaggag tccaaatacc agagaatgtt ttagatacac catcaaaaat tgtataaagt    5280
ggctctaact tatcccaata acctaactct ccgtcgctat tgtaaccagt tctaaaagct    5340
gtatttgagt ttatcaccct tgtcactaag aaaataaatg cagggtaaaa tttatatcct    5400
tcttgttta tgtttcggta taaaacacta atatcaattt ctgtggttat actaaaagtc     5460
```

```
gtttgttggt tcaaataatg attaaatatc tcttttctct tccaattgtc taaatcaatt   5520
ttattaaagt tcatttgata tgcctcctaa attttatct aaagtgaatt taggaggctt    5580
acttgtctgc tttcttcatt agaatcaatc cttttttaaa agtcaatatt actgtaacat   5640
aaatatatat tttaaaaata tcccacttta tccaattttc gtttgttgaa ctaatgggtg   5700
ctttagttga agaataaaga ccacattaaa aaatgtggtc ttttgtgttt ttttaaagga   5760
tttgagcgta gcgaaaaatc cttttcttc ttatcttgat aataagggta actattgccg    5820
atgataagct gtcaaacatg agaattggcc ttaagggcct gct                    5863

<210> SEQ ID NO 7
<211> LENGTH: 25
<212> TYPE: DNA
<213> ORGANISM: Artificial sequence
<220> FEATURE:
<223> OTHER INFORMATION: Primer Cat,aa49,forw

<400> SEQUENCE: 7
cctttattaa tgaatttcc tgctg                                         25

<210> SEQ ID NO 8
<211> LENGTH: 26
<212> TYPE: DNA
<213> ORGANISM: Artificial sequence
<220> FEATURE:
<223> OTHER INFORMATION: Primer GFP,aa17,rev

<400> SEQUENCE: 8
caacaagaat tgggacaact ccagtg                                       26

<210> SEQ ID NO 9
<211> LENGTH: 39
<212> TYPE: DNA
<213> ORGANISM: Artificial sequence
<220> FEATURE:
<223> OTHER INFORMATION: Primer 491264

<400> SEQUENCE: 9
tttattacgc gtcaagagga ggttgttttt gtcatgatc                         39

<210> SEQ ID NO 10
<211> LENGTH: 36
<212> TYPE: DNA
<213> ORGANISM: Artificial sequence
<220> FEATURE:
<223> OTHER INFORMATION: Primer 492902

<400> SEQUENCE: 10
tttattaagc ttatccccca caacgatttt cctgtc                            36

<210> SEQ ID NO 11
<211> LENGTH: 43
<212> TYPE: DNA
<213> ORGANISM: Artificial sequence
<220> FEATURE:
<223> OTHER INFORMATION: Primer 491266

<400> SEQUENCE: 11
ttatttacgc gtaaggtatg ggggatggg gatgaaaaaa tgg                     43

<210> SEQ ID NO 12
<211> LENGTH: 37
<212> TYPE: DNA
<213> ORGANISM: Artificial sequence
```

-continued

```
<220> FEATURE:
<223> OTHER INFORMATION: Primer 492903

<400> SEQUENCE: 12
ttatttaagc ttcagctcgg cgaaggattg taacaac                                    37
```

DNASE EXPRESSION IN RECOMBINANT HOST CELLS

CROSS-REFERENCE TO RELATED APPLICATIONS

This application is a continuation of U.S. application Ser. No. 12/516,720 filed May 28, 2009, now U.S. Pat. No. 8,227,227, which is a 35 U.S.C. 371 national application of PCT/EP2007/063109 filed Nov. 30, 2007, which claims priority or the benefit under 35 U.S.C. 119 of Danish application no. PA 2006 01581 filed Nov. 30, 2006 and U.S. provisional application No. 60/870,156 filed Dec. 15, 2006, the contents of which are fully incorporated herein by reference.

SEQUENCE LISTING

The present invention comprises a sequence listing.

FIELD OF THE INVENTION

The present invention relates to recombinant host cells capable of producing various recombinant polypeptides, in particular enzymes, essentially free from contaminating DNA, as well as methods of producing said polypeptides essentially free from contaminating DNA.

BACKGROUND OF THE INVENTION

Many *Bacillus* production strains are used for recombinant production of enzymes, and there are often regulatory restrictions concerning the presence of recombinant DNA in the final enzyme product.

A nuclease-encoding gene from *Staphylococcus aureus* was integrated into the genomes of several Poly(3-hydroxy-alkanoates; PHA) producers and expressed, in order to express the nuclase and thereby reduce the otherwise high viscosity of cell-lysates due to the presence of chromosomal DNA. Staphylococcal nuclease was readily expressed in PHA-producing *Pseudomonas* strains and was directed to the periplasm, and occasionally to the culture medium, without affecting PHA production or strain stability [Zhuang et al. Reduction of Cell Lysate Viscosity during Processing of Poly (3-Hydroxyalkanoates) by Chromosomal Integration of the Staphylococcal Nuclease Gene in *Pseudomonas putida*. Appl Environ Microbiol. 1999 April; 65(4): 1524-1529].

The phosphate-starvation stimulon of *Bacillus licheniformis* has been analyzed at the transcriptional and translational level. It was shown that *B. licheniformis* has evolved its own strategies to cope with this nutrient limitation. By means of the secretome analysis a phytase was identified as the most abundant protein under phosphate-starvation conditions. Data of this study indicate that, unlike in *B. subtilis*, phosphate starvation in *B. licheniformis* does not induce the SigmaB-dependent general stress response (Hoi et al. The phosphate-starvation response of *Bacillus licheniformis*. 2006. Proteomics, Vol. 6 (12) pp. 3582-3601).

During phosphate starvation, *Bacillus subtilis* regulates genes in the PhoP regulon to reduce the cell's requirement for this essential substrate and to facilitate the recovery of inorganic phosphate from organic sources such as teichoic and nucleic acids. Among the proteins that are highly induced under these conditions is PstS, the phosphate-binding lipoprotein component of a high-affinity ABC-type phosphate transporter. PstS is encoded by the first gene in the pst operon, the other four members of which encode the integral membrane and cytoplasmic components of the transporter (Allenby et al. 2004. Post-transcriptional regulation of the *Bacillus subtilis* pst operon encoding a phosphate-specific ABC transporter. Microbiol 150 (Pt 8) pp. 2619-2628.

SUMMARY OF THE INVENTION

It is an object of the present invention to provide recombinant host cells capable of producing various products, in particular enzymes, essentially free from DNA, as well as methods of producing various products essentially free from DNA, and methods for constructing said recombinant host cells.

A recombinant *Bacillus* host cell was successfully engineered to express a recombinant nuclease (DNase) during fermentation, particularly towards the end of the fermentation.

We have cloned and expressed extracellular DNases from both *Bacillus subtilis* and *Bacillus licheniformis* that allow very efficient degradation of DNA. The gene nucB coding for this extracellular DNase (nuclease) from *B. subtilis* and *B. licheniformis* was cloned downstream of the pstS promoter. The pstS promoter is regulated by the level of phosphate in the medium during fermentation in a way where the promoter is activated by low levels of phosphate and blocked by high levels of phosphate.

Initially, flourescent protein GFP was used as a marker for expression from the pstS promoter, and it was shown that this particular promoter is very tightly controlled during fermentation. Since most *Bacillus* fermentations are entering a late phase where the level of phosphate is low, the expression of the nucB gene by the pstS promoter could be activated at the end of fermentation and express the nuclease when it is needed for cleaning the fermentation broth for excess DNA.

We show herein that an expression cassette consisting of the pstS promoter and nucB gene inserted into the chromosome of *B. subtilis* is regulated by the level of phosphate in shake flasks and 1 liter scale. In the presence of phosphate in the growth medium, the fermentation supernatant was not able to degrade added DNA. However, in a growth medium that was phosphate depleted by fermentation, a very efficient degradation of added DNA by the supernatant was observed, thus demonstrating the presence of nuclease in the supernatant. In this way we successfully separated the enzyme expression phase and the expression of the nuclease to avoid interference with enzyme productivity.

Accordingly, a first aspect of the invention relates to a cell producing at least one polypeptide of interest and expressing one or more recombinant nuclease encoding gene(s) thereby producing the nuclease(s).

In a second aspect, the invention relates to a method for producing a polypeptide of interest essentially free from contaminating DNA, said method comprising the steps of:
(a) cultivating a cell that produces at least one polypeptide of interest and expresses one or more recombinant nuclease encoding gene(s) thereby producing the nuclease(s); and
(b) isolating the polypeptide of interest.

BRIEF DESCRIPTION OF DRAWINGS

FIG. 9. Shows the analysis of supernatants for Dnase, from different amylase-production strains comprising nucB: MOL2716, MOL2717, MOL2718; the fermentations are in TY-medium:
Lane 1: Marker DNA
Lane 2: Marker DNA+MOL2716 strain (+phosphate)
Lane 3: Marker DNA+MOL2717 strain (+phosphate)
Lane 4: Marker DNA+MOL2718 strain (+phosphate)
Lane 5: Marker DNA+MOL2684 strain (+phosphate)
Lane 6: Marker DNA+Sm-30 strain (+phosphate)
Lane 7: Marker DNA+MOL2716 strain (−phosphate)
Lane 8: Marker DNA+MOL2717 strain (−phosphate)
Lane 9: Marker DNA+MOL2718 strain (−phosphate)
Lane 10: Marker DNA+MOL2684 strain (−phosphate)
Lane 11: Marker DNA+Sm-30 strain (−phosphate)
Lane 12: Marker DNA FIG. 10. Shows the analysis of supernatants for Dnase, from the amylase-production strain comprising nucB: MOL2717; the fermentations were in 1 liter scale, phosphate limited.
Lane 1: Marker DNA
Lane 2: Marker DNA+MOL2717 strain, 1 liter fermentation (−phosphate), 1. day
Lane 3: Marker DNA+MOL2717 strain, 1 liter fermentation (−phosphate), 2. day
Lane 4: Marker DNA+MOL2717 strain, 1 liter fermentation (−phosphate), 3. day
Lane 5: Marker DNA+MOL2717 strain, 1 liter fermentation (−phosphate), 4. day
Lane 6: Marker DNA+MOL2717 strain, 1 liter fermentation (−phosphate), 5. day
Lane 7: Marker DNA+MOL2717 strain, TY medium (−phosphate), overnight
Lane 8: Marker DNA+MOL2684 strain, TY medium (−phosphate), overnight
Lane 9: Marker DNA+Sm-30 strain, TY medium (−phosphate), overnight
Lane 10: Marker DNA+MOL2717 strain, PS1 medium, 7 days
Lane 11: Marker DNA+MOL2684 strain, PS1 medium, 7 days
Lane 12: Marker DNA+Sm-30 strain, PS1 medium, 7 days
Lane 13: Marker DNA

DETAILED DESCRIPTION OF THE INVENTION

Figure 1:
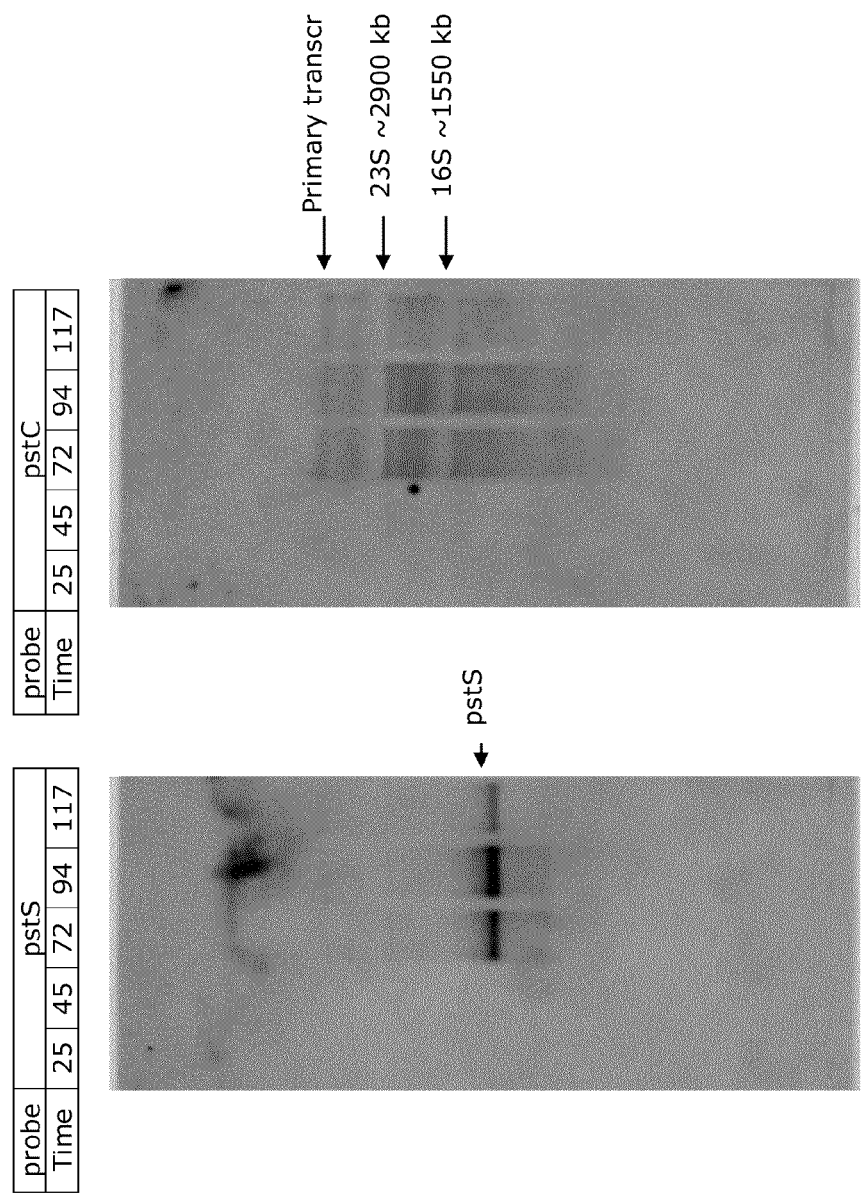
FIG. 1. A Northern blot showing expression of the pst-operon during a fermentation. The pst-operon in *B. licheniformis* consists of five genes (as in *B. subtilis*): pstS/C/A/BA/BB. The regulation seems to be the same as in *B. subtilis*, where the pst-operon is transcribed as a 4.4 kb primary transcript and is rapidly processed into smaller products, including a stable 0.9 kb pstS transcript.

The first aspect of the invention relates to a cell producing at least one polypeptide of interest and expressing one or more recombinant nuclease encoding gene(s) thereby producing the nuclease(s).

Host cell: The term "host cell" or "cell", as used herein, includes any cell type which is susceptible to transformation, transfection, transduction, and the like with a nucleic acid construct comprising a polynucleotide of the present invention.

Host Cells

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular microorganisms are bacterial cells such as gram positive bacteria including, but not limited to, a *Bacillus* cell, e.g., *Bacillus alkalophilus*, *Bacillus amyloliquefaciens*, *Bacillus brevis*, *Bacillus circulans*, *Bacillus clausii*, *Bacillus coagulans*, *Bacillus lautus*, *Bacillus lentus*, *Bacillus licheniformis*, *Bacillus megaterium*, *Bacillus stearothermophilus*, *Bacillus subtilis*, and *Bacillus thuringiensis*; or a *Streptomyces* cell, e.g., *Streptomyces lividans* and *Streptomyces murinus*, or gram negative bacteria such as *E. coli* and *Pseudomonas* sp. In a preferred aspect, the bacterial host cell is a *Bacillus lentus*, *Bacillus licheniformis*, *Bacillus stearothermophilus*, or *Bacillus subtilis* cell. In another preferred aspect, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred aspect, the yeast host cell is a *Candida, Hansenula, Kluyveromyces, Pichia, Saccharomyces, Schizosaccharomyces*, or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Coprinus, Coriolus, Cryptococcus, Filobasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa*, or *Ceriporiopsis subvermispora, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

In a preferred embodiment of the invention, the cell is a Gram-positive cell, preferably a *Bacillus* cell; and most preferably a *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, or *Bacillus thuringiensis* cell.

Isolated polypeptide: The term "isolated polypeptide" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

Substantially pure polypeptide: The term "substantially pure polypeptide" denotes herein a polypeptide preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation.

The polypeptides of the present invention are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

Herein, the term "substantially pure polypeptide" is synonymous with the terms "isolated polypeptide" and "polypeptide in isolated form."

In a preferred embodiment of the first and second aspects, the at least one polypeptide of interest comprises an enzyme, preferably the enzyme is a lyase, a ligase, a hydrolase, an oxidoreductase, a transferase, or an isomerase.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form. In particular, it is preferred that the polynucleotides disclosed herein are in "essentially pure form", i.e., that the polynucleotide preparation is essentially free of other polynucleotide material with which it is natively associated. Herein, the term "substantially pure polynucleotide" is synonymous with the terms "isolated polynucleotide" and "polynucleotide in isolated form." The polynucleotides may be of genomic, cDNA, RNA, semisynthetic, synthetic origin, or any combinations thereof.

cDNA: The term "cDNA" is defined herein as a DNA molecule which can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA which is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polynucleotide encoding a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG. The coding sequence may a DNA, cDNA, or recombinant nucleotide sequence.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the invention, and which is operably linked to additional nucleotides that provide for its expression.

A polypeptide of the present invention may be a bacterial polypeptide. For example, the polypeptide may be a gram positive bacterial polypeptide such as a *Bacillus* polypeptide, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis*, or *Bacillus thuringiensis* polypeptide; or a *Streptomyces* polypeptide, e.g., a *Streptomyces lividans* or *Streptomyces murinus* polypeptide; or a gram negative bacterial polypeptide, e.g., an *E. coli* or a *Pseudomonas* sp. polypeptide.

A polypeptide of the present invention may also be a fungal polypeptide, and more preferably a yeast polypeptide such as a *Candida, Kluyveromyces, Pichia, Saccharomyces, Schizosaccharomyces*, or *Yarrowia* polypeptide; or more preferably a filamentous fungal polypeptide such as an *Acremonium, Aspergillus, Aureobasidium, Cryptococcus, Filobasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium*, or *Trichoderma* polypeptide.

In another preferred aspect, the polypeptide is an *Aspergillus aculeatus, Aspergillus awamori, Aspergillus fumigatus, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum,*

*Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei,* or *Trichoderma viride* polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of another microorganism. Once a polynucleotide sequence encoding a polypeptide has been detected with the probe(s), the polynucleotide can be isolated or cloned by utilizing techniques which are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligated activated transcription (LAT) and nucleotide sequence-based amplification (NASBA) may be used.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the polypeptide encoding region of SEQ ID NO: 1, e.g., a subsequence thereof, and/or by introduction of nucleotide substitutions which do not give rise to another amino acid sequence of the polypeptide encoded by the nucleotide sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

The present invention also relates to nucleic acid constructs comprising an isolated polynucleotide of the present invention operably linked to one or more control sequences which direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence which is recognized by a host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the*

*National Academy of Sciences USA* 80: 21-25). Further promoters are described in "Useful proteins from recombinant bacteria" in *Scientific American,* 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1,ADH2/GAP), *Saccharomyces cerevisiae* triose phosphate isomerase (TPI), *Saccharomyces cerevisiae* metallothionine (CUP1), and *Saccharomyces cerevisiae* 3-phosphoglycerate kinase. Other useful promoters for yeast host cells are described by Romanos et al., 1992, Yeast 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C(CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described above may be joined together to produce a recombinant expression vector which may include one or more convenient restriction sites to allow for insertion or substitution of the nucleotide sequence encoding the polypeptide at such sites. Alternatively, a nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

A conditionally essential gene may function as a non-antibiotic selectable marker. Non-limiting examples of bacterial conditionally essential non-antibiotic selectable markers are the dal genes from *Bacillus subtilis*, *Bacillus licheniformis*, or other *Bacilli*, that are only essential when the bacterium is cultivated in the absence of D-alanine. Also the genes encoding enzymes involved in the turnover of UDP-galactose can function as conditionally essential markers in a cell when the cell is grown in the presence of galactose or grown in a medium which gives rise to the presence of galactose. Non-limiting examples of such genes are those from *B. subtilis* or *B. licheniformis* encoding UTP-dependent phosphorylase (EC 2.7.7.10), UDP-glucose-dependent uridylyl-transferase (EC 2.7.7.12), or UDP-galactose epimerase (EC 5.1.3.2). Also a xylose isomerase gene such as xylA, of *Bacilli* can be used as selectable markers in cells grown in minimal medium with xylose as sole carbon source. The genes necessary for utilizing gluconate, gntK, and gntP can also be used as selectable markers in cells grown in minimal medium with gluconate as sole carbon source. Other examples of conditionally essential genes are known in the art. Antibiotic selectable markers confer antibiotic resistance to such antibiotics as ampicillin, kanamycin, chloramphenicol, erythromycin, tetracycline, neomycin, hygromycin or methotrexate.

Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyl-transferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, Gene 98:61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

In a preferred embodiment of the invention, the one or more recombinant nuclease encoding gene(s) is integrated into the genome of said cell. This may be achieved as outlined herein or as disclosed in WO 2002/000907.

In another preferred embodiment of the invention the one or more recombinant nuclease encoding gene(s) is transcribed from a regulated promoter that is at least 10% upregulated, preferably at least 20%, 30%, 40%, 50%, 60%, 70%, 80%, 90%, 100% or more upregulated, during the time of a standard fed-batch fermentation of said cell, even more preferably the promoter is upregulated in response to a substance-limitation in the growth medium, most preferably the promoter is upregulated in response to phosphate-limitation in the growth medium.

In a most preferred embodiment of the invention, the one or more recombinant nuclease encoding gene(s) is transcribed from the pstS promoter of *B. licheniformis* or *B. subtilis*.

Methods of Production

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

EXAMPLES

When following gene regulation in lab. scale fermentations using DNA microarrays, a number cellular responses are seen as a consequence of the changing fermentation medium.

Example 1

Phosphate Starvation Response in *B. Licheniformis*

Phosphate starvation in late stage fermentation samples was detected already in our first microarray experiments, using partial *B. licheniformis* microarray slides containing about 200 interesting genes. Cells are not "truly" limited for phosphate, since huge amounts of phosphate is normally incorporated into teichoic acids in the cell wall. When the cells sense a low concentration of phosphate in the medium, one of the responses is to substitute these teichoic acids with non-phosphate containing teichuronic acids and thereby liberate phosphate.

Making a biosensor for phosphate limitation could therefore be questioned, if only one biosensor was planned to be made. However, in combination with biosensors for different trace metals, the phosphate starvation biosensor is essential, as discussed above. A number of other facts also made the phosphate biosensor a very attractive choice to start with:

1) the pst-operon (involved in high affinity uptake of phosphate) is very tightly regulated, i.e. the background level of transcription in cells that are not starved for phosphate is minimal and the transcription is very high when the cells are subjected to phosphate starvation (see FIG. 1).

2) Another gene that is induced during phosphate starvation is the phoD gene, which encodes an alkaline phosphatese/phosphodiesterase. The activity of this alkaline phosphatase is easy to measure (colorless paranitrophenol is hydrolyzed to free paranitrophenol, which is colored yellow) and thus gives a possibility to confirm results seen with the pstS-GFP fusion.

3) Inorganic phosphate concentrations are easily determined with commercial kits or by HPCE. The reason for this is that phosphate is a major bioelement and phosphate starvation is induced already at about 0.5 g/L.

Example 2

Strain Construction in *Bacillus* for Detecting Phosphate Starvation

When the phosphate level is low the transcription of certain genes responds strongly. A set of such genes are found in the pst operon of *Bacillus*. In our experiment a gene encoding a variant of the green fluorescent protein, denoted BioST (variant: F64L, S65T), from the jellyfish Aequorea victoria, has been fused transcriptionally to the pst transcript [New Unstable Variants of Green Fluorescent Protein for studies of Transient gene expression in bacteria. App. Env. Mic. 1998 p2240-2246, incorporated herein by reference].

Constructs were made, wherein the bioST gene was inserted 1) immediately downstream of the pst promoter region and upstream of the pst operon "Ppst bioST", or 2) downstream of the last gene in the operon (pstBB) in the transcript "pstBB bioST".

The Ppst bioST fusion was inserted into the chromosome of *B. subtilis* in the amyE locus (PP2203-1), and in *B. licheniformis* the fusion gene was inserted in the bglC gene (PP2244), using standard methods.

The pstBB bioST transcriptional fusion was inserted into the pst operon in the chromosome of another *B. subtilis* strain (PP2216-1), using standard methods.

The DNA sequences used in the pst constructs in *B. subtilis* was from the published *B. subtilis* 168 genome. The DNA sequences used in the pst constructs in *B. licheniformis* were isolated from a proprietary *B. licheniformis* Si3 strain.

The terminator behind bioST in both PP2203-1 and PP2244-1 is the aprH terminator from *B. clausii*. In the C-terminal insertion of bioST in PP2216-1 the terminator is the original terminator of the pst operon.

In the above strains the GFP accumulation may be a disadvantage to see what's going on in fermentation in the present moment—as the first step in that direction we made a BioST variant with an instability tag, the ssrA tag, which directs the cytoplasmatic peptides towards the clpX clpP degradation complex.

The ssrA tag from *B. subtilis* is known to be GKTNSFN-QNVALLA. And the homologue from *B. licheniformis* Si3 is VKTHLNITGKSNQNLALAA.

A *B. subtilis* strain with the C-terminal *B. subtilis* ssrA tag on BioST was made. The GFP accumulation in *B. subtilis* PP2239-1 is much lower than the parallel PP2203-1 strain run under same conditions.

Resulting Strains:
PP2203-1: *B. subtilis* 168 aprE, nprE, amyE:(cat)PpstbioST.
PP2216-1: *B. subtilis* 168 aprE, nprE, pstBB+::bioST.
PP2244-1: *B. licheniformis* Si3 aprL, bglC::Ppst bioST.
PP2239-1: *B. subtilis* 168 aprE, nprE, amyE:(cat)Ppst bioST_ssrA.

Example 3

On-Line Measurement of Phosphate Starvation

Equipment
1) A spectrometer, which detects all emission wavelengths between 329-1100 nm (AVANTES™ AVASPEC™-2048FT-SPU), coupled via an via an optic cable (AVANTES™ FC-UV600-2) to a collimating lens situated in a light protected box (see below). BioST emission maximum is at about 508 nm
2) A light source, which gives a strong excitation light at about 470 nm and no light at all at wavelengths above 500 nm, since reflection of the excitation light into the spectrometer will disturb detection of the emission light of the GFP protein (BioST excitation maximum is at about 470 nm). We tested the AVANTES™ AVALIGHT™-LED-470 nm, with an optical bandpass filter (470+/−10 nm from KNIGHT OPTICAL™ (UK) Ltd), but found the light intensity too low. Instead we used a home-made light source, which consists of a 5 mm high brightness blue LED (2000 mcd, peak wavelength of 470 nm), combined with the abovementioned optical filter. The LED was placed in the light protected box, very close to the flow-through cuvette.
3) A flow-through cuvette, through which fermentation broth is passed and then re-circulated back to the tank. The circulation is driven by a peristaltic pump.
4) A light-protected box (home-made), where the flow-through cuvette, the collimating lens, and the light source are mounted in angles that result in maximal detection of the emission signal.

Results with the *B. Subtilis* Strain PP2203-1 (pstS-GFP Fusion in the amyE Locus)

To be able to use a biosensor for fermentation regulation, a number of important criteria have to be fulfilled:
1) it must be possible to detect the signal of the cellular response to the starvation condition very soon after the cells first sense the starvation.
2) the whole population should react in the same manner, so that regulation is not based on a reaction occurring in a sub-population of the cells.
3) The increase in signal should be shut off as soon as the starvation condition is terminated by addition of the limiting nutrient To determine if these criteria could be fulfilled, we started a fermentation with a low phosphate concentration and took out samples each hour for nine hours for different analyses:
1) pstS and pstS-GFP mRNA levels determinations using Northern blot,
2) off-line GFP concentration determinations,
3) alkaline phosphatase activity determinations,
4) FACS analysis,
5) Inorganic phosphate concentration determinations.

Figure 2:
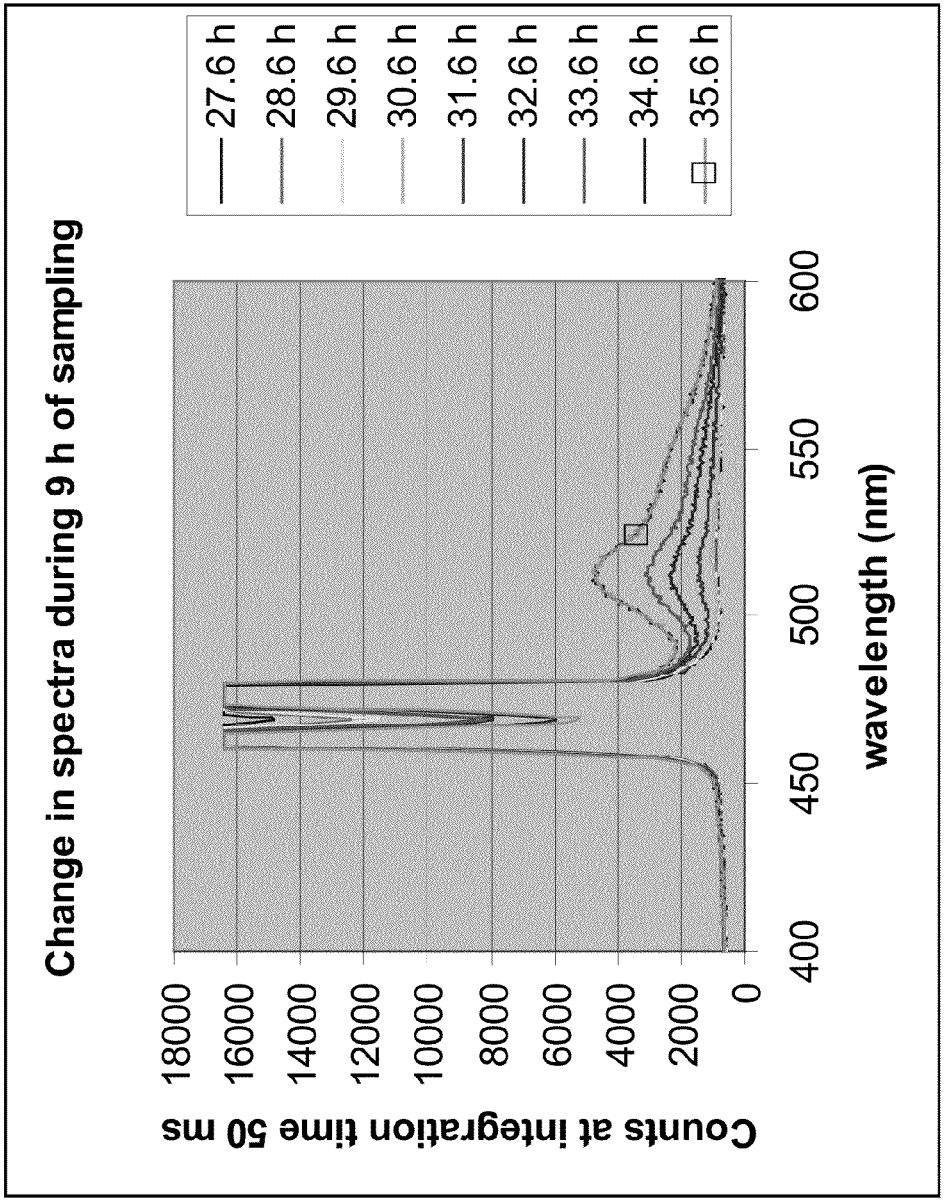
FIG. 2. Change in on-line emission spectra during 9 h of sampling in a fermentation, starting 4 hours before induction of phosphate starvation (for simplicity, one spectrum per hour is shown in this graph, but data was collected once every 10 minutes during the experiment). The peak at 460 to 480 nm is a reflection of the excitation light and the peak at 508 nm that increases with time is the GFP emission signal.

The sampling was started four hours before we detected a signal of phosphate starvation. FIG. 1 shows how the spectra change during these nine hours. FIG. 2 show the data collected during these nine hours and the simultaneous increase in GFP signal (both on-line and off-line) and in alkaline phosphatase activity.

Figure 3:
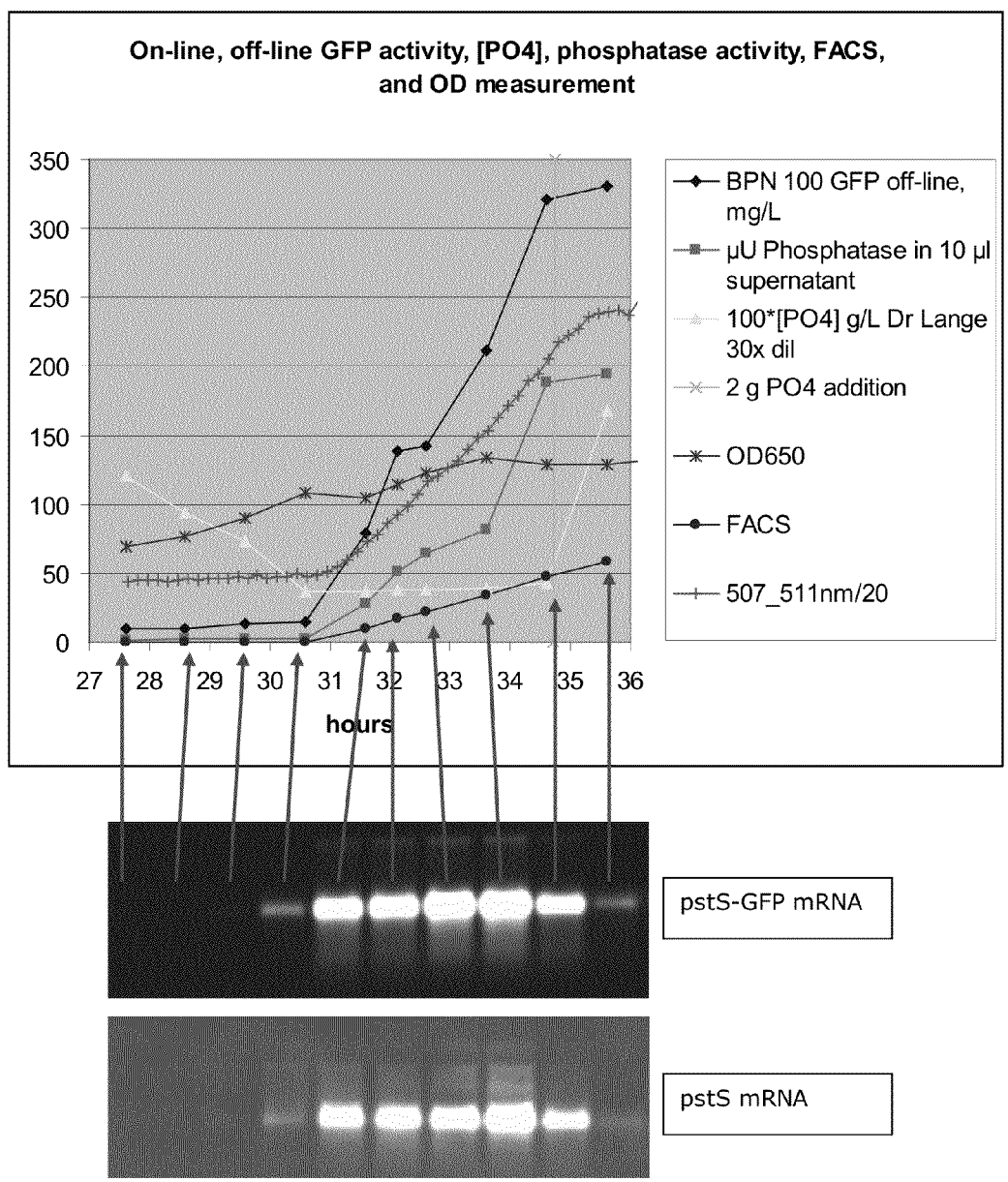
FIG. 3. Data from samples taken out from a fermentation over a period of nine hours, showing on-line and off-line GFP determinations, growth of biomass, phosphate concentration, FACS analysis, alkaline phosphatase activity, and mRNA levels of the native pstS mRNA and the pstS-GFP fusion mRNA.

FACS analysis and microscopic examination of the samples showed induction of GFP production at the same time point, and very importantly, also showed that the whole population of cells reacted in the same manner (see FIG. 3).

Figure 4:
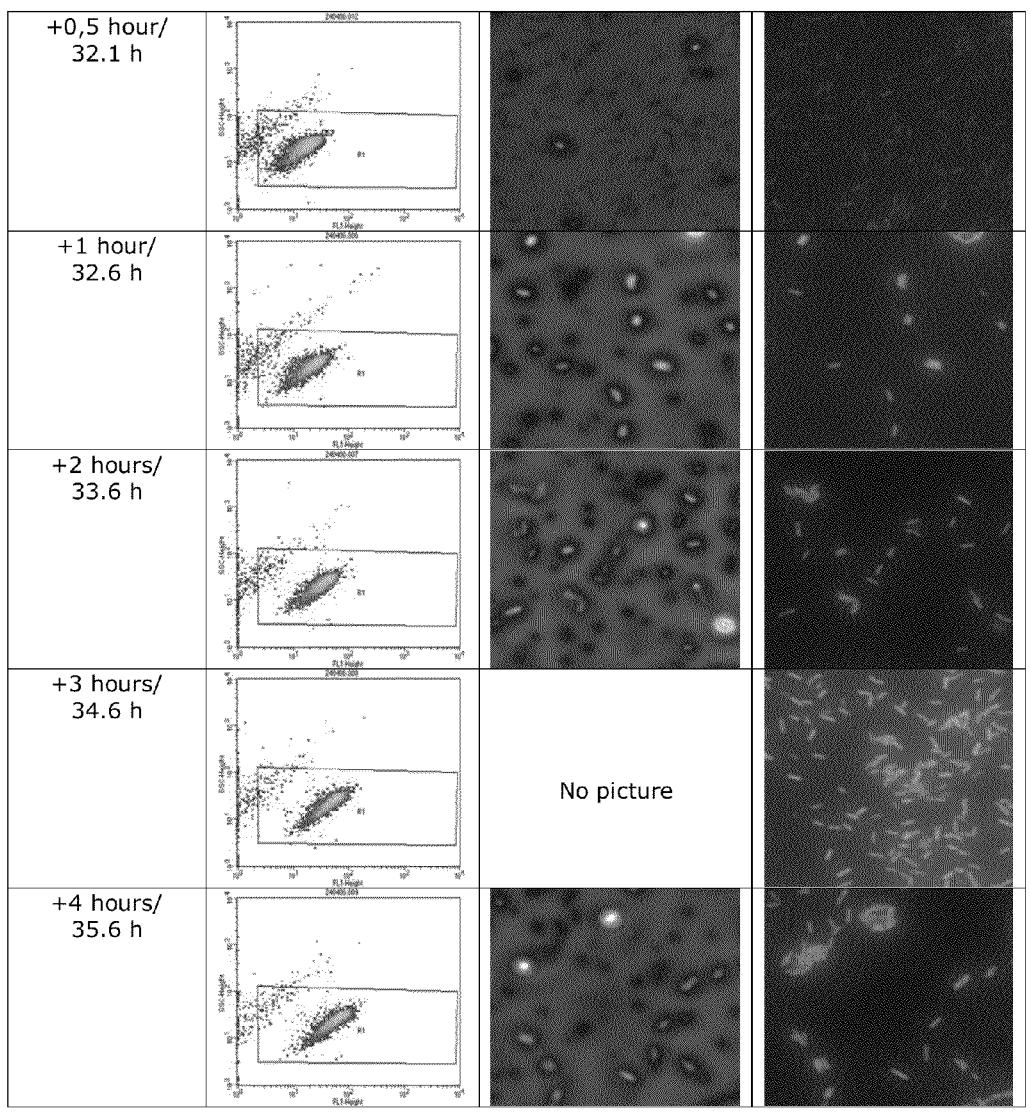
FIG. 4. FACS analysis and microscopic examination of samples taken before and during induction of a phosphate starvation response showing that the whole population induce GFP expression (see FIG. 2 for comparison to on-line and off-line GFP data). Column A) shows the FACS analysis; the Y-axes in the FACS graphs show the sideward scatter (reflection of excitation light measured at wavelength 488+/−10 nm), which is a measure of cell size (or of size of any particle present in the medium); the X-axes show the intensity of the fluorescence at 530+/−30 nm (FL1). The light source is a blue laser (wavelength 488 nm). Columns B and C show microscopy pictures of the samples using a phase-contrast and a fluorescence microscope.
Figure 5:
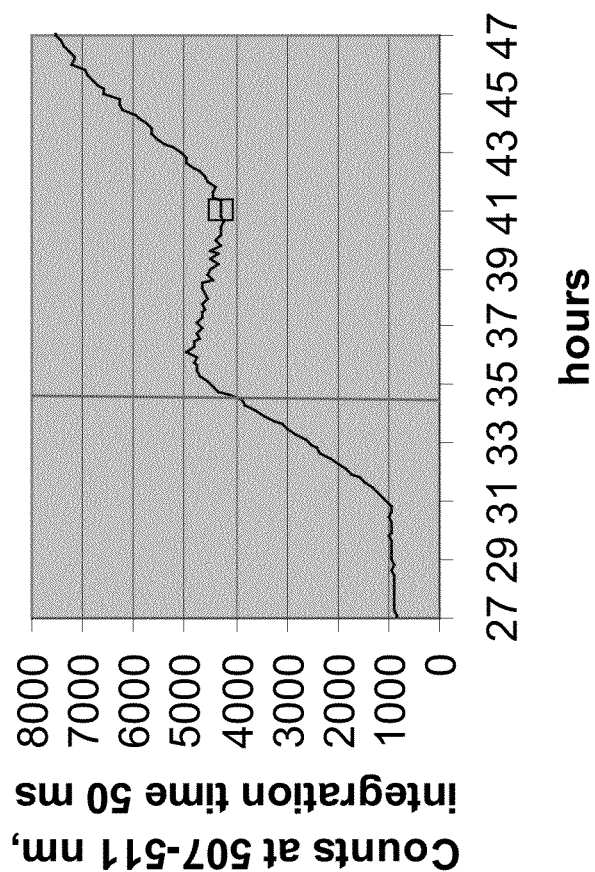
FIG. 5. On-line measurement of GFP emission in fermentation BPN100 (values at 507-511 nm). Phosphate starvation starts at 31 h and the GFP signal increases (31-36 h) until about one hour after addition of phosphate. The added phosphate is probably consumed at about 42 h where the GFP signal again starts to increase.

Most importantly, Northern blots showed that the pstS and the pstS-GFP are totally co-regulated, that we observe the GFP very shortly after we first detect the induction at the mRNA level, and finally, that addition of phosphate shuts off transcription of the promoter rapidly. Shutting down the promoter with phosphate also results in a stop in production of GFP about one hour after addition. This delay is probably an effect of a fairly stable pstS-GFP mRNA (a 5 to 10-fold reduction in pstS-GFP levels in 52 minutes after phosphate addition). FIG. 4. shows the on-line data on the change in GFP emission during 20 hours after sampling start. Here we see that the signal intensity stops to increase after about one hour after phosphate addition and that the intensity slowly drops. The added phosphate is probably consumed at about 42 h where the GFP signal again starts to increase.

Figure 6:
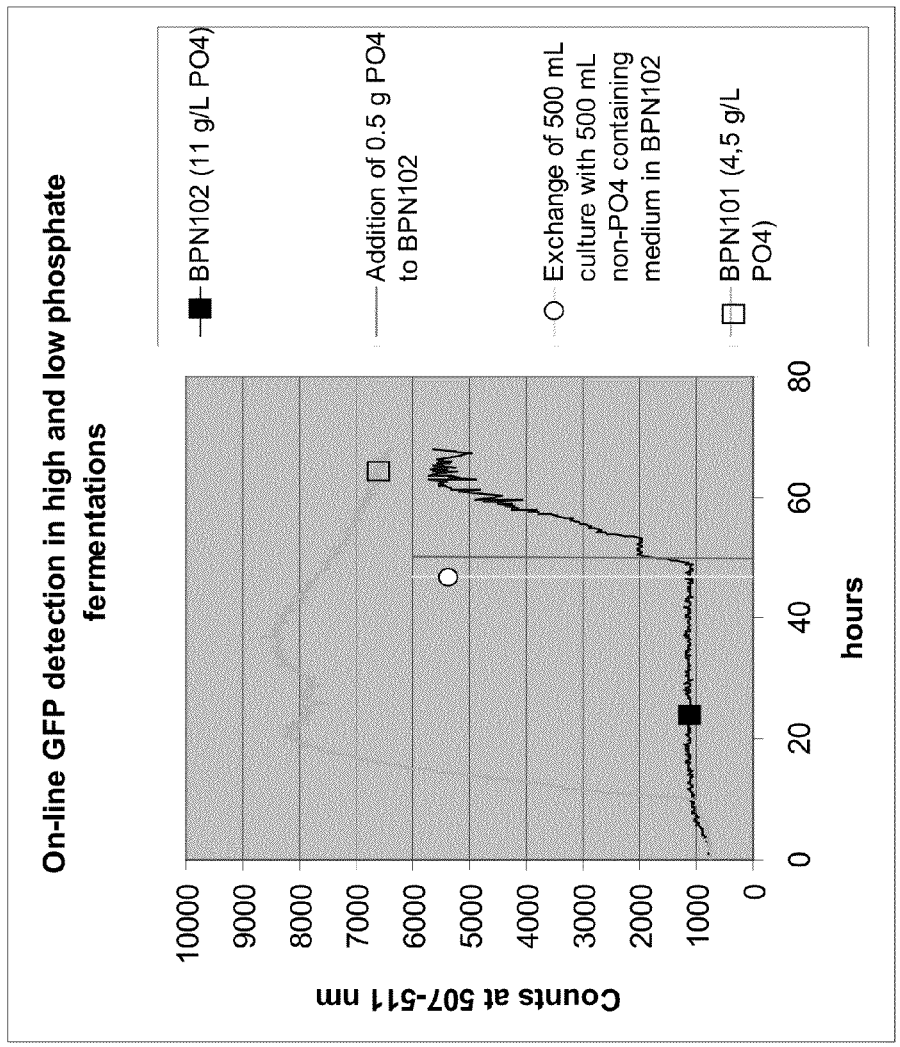
FIG. 6. On-line measurement of GFP emission in fermentations BPN101 and BPN102 (values at 507-511 nm). Phosphate starvation is detected after 10 hours in BPN101, while no induction is seen in the high phosphate fermentation until half of the fermentation broth is substituted with a medium lacking phosphate. This induces an increase in GFP emission, which is halted for three hours by addition of 0.5 g phosphate.

To ensure that high biomass concentrations would not disturb the GFP signal, two more fermentations were run where one started with a low phosphate concentration (BPN102) and one with a high phosphate concentration (BPN101). The results are shown in FIG. 6. No GFP induction occurs in BPN101, while a rapid GFP induction is seen in BPN102.

To test if we could induce a phosphate starvation in BPN101, about half the volume of the tank was exchanged with a medium that lacked phosphate at 47 hours into the fermentation. Shortly after, an increase in GFP signal was seen and 0.5 g phosphate was added. This stopped GFP production for 3 h and then, when the added phosphate was consumed, the GFP signal started to increase again.

Example 4

A Xylose-Induced Expression System for *Bacillus licheniformis*

Xylose utililization in *B. subtilis* requires the production of xylose isomerase (XyIA) and xylulose kinase (XyIB) and is regulated at the level of transcription by a xylose-responsive repressor protein encoded by xylR and by catabolite repression. Genes xylR and xylAB are divergently transcribed from a common intergenic region containing xyl operator sequences which are bound by xylR in the absence of an inducer. The xylose operon of *B. subtilis* is a well-characterized regulatory system with tight transcriptional regulation. Bhaysar et al (2001) developed a xylose-dependent system for expression of cloned genes from the amyE locus in *B. subtilis*. We have constructed a similar system for expression of cloned genes from the xyl locus in *B. licheniformis* Si3 strains.

The xylose locus was amplified from the chromosome of *B. licheniformis* Si3 and sequenced. Two regions were selected as targets for integration in the chromosome by double homologous recombination events. The upstream region (xyl-us) includes the 5'-end of the gene encoding the xylose repressor (xylR), intergenic xyl operator sequences, the xylA promoter, and the 5'-end of xylA encoding 21 aa followed by an artificial stop codon. The downstream region (xyl-ds) includes a xylB intragenic region.

The expression cassette contains four unique restriction sites but no Shine-Dalgarno sequence for translation of the cloned gene.

A gene selected for cloning and xylose-dependent expression therefore needs to bring its own Shine-Dalgarno sequence. This can easily be achieved by careful primer design and PCR amplification, the upstream primer should have an extra sequence with a recognition site for cloning, the SD-sequence, and the start codon for the gene to be expressed. The downstream primer should contain a stop codon but not a terminator sequence since this would prevent co-expression with the GFP-encoding BioST expression reporter-gene in the construct.

Figure 7:
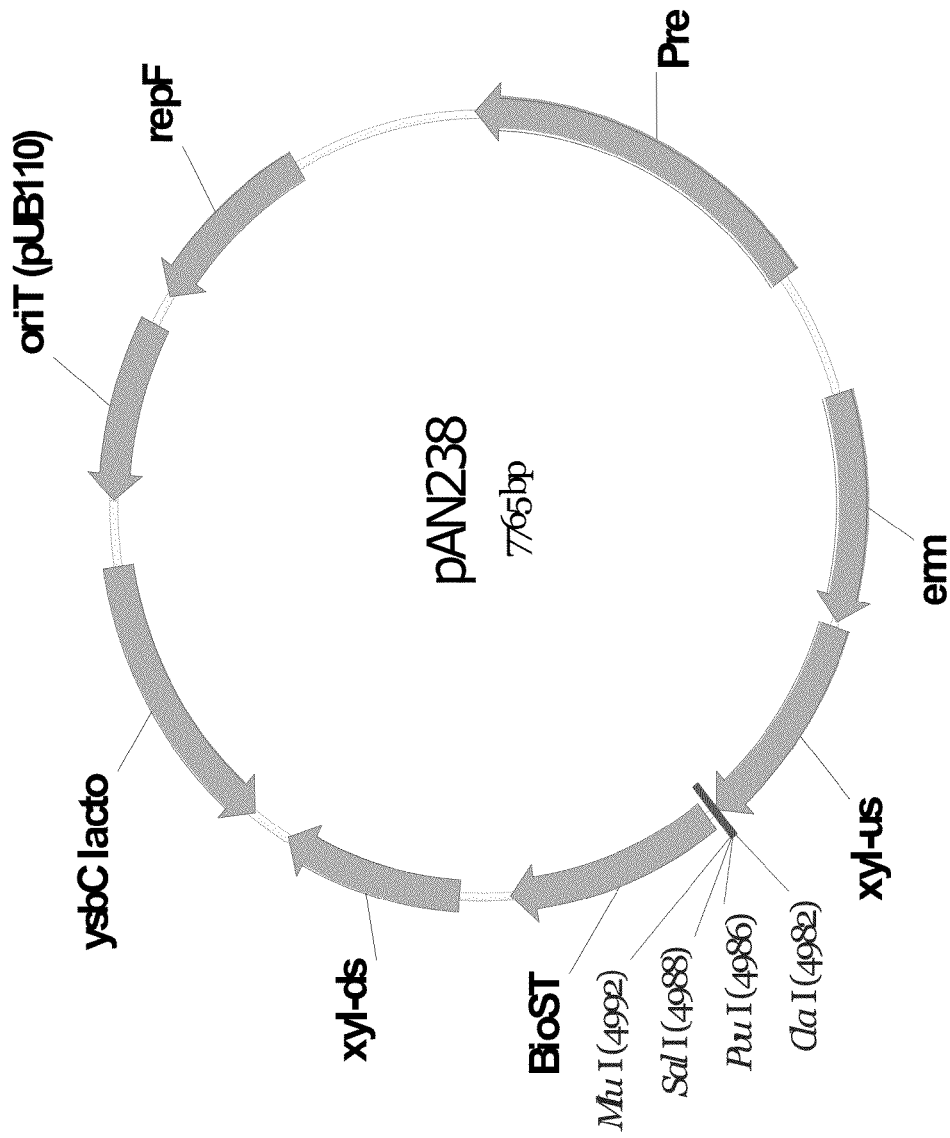
FIG. 7. A xylose-induced integrative cloning vector expression system for *Bacillus licheniformis* denoted pAN238, the full DNA sequence of this plasmid is shown in SEQ ID NO: 1.

The resulting cloning expression vector was denoted pAN238 (FIG. 7), cloning of an amplified "gene X" in pAN238 ensures its co-expression with BioST. Integration of the expression cassette into the chromosome of *B. licheniformis* by a double cross-over event will restore xylR but inactivate xylAB by serious truncation. The cloned gene will be expressed in the presence of xylose together with BioST. The full DNA sequence of pAN238 is provided in SEQ ID NO: 1.

Example 4

Xylose Induced Nuclease Expression in *B. Licheniformis*

In the first cloning strategy we inserted both nucB genes each into the pAN238 vector designed for integration into the xyl locus in *B. licheniformis*.

This integration allowed for induction of the nucB expression by adding xylose to the medium, since the nucB gene is under control of the xyl promoter. However, as a free plasmid in *B. subtilis* the xyl promoter will be constitutively active because the XylR repressor is out-titrated and it was expected that nucB would be fully expressed under these conditions. The two nucB genes were each amplified by PCR and cloned into the plasmid.

```
PCR on B. licheniformis nucB:
Primer 480596 (SEQ ID NO: 2):
TTTATTATCGATCAAGAGGAGGTTGTTTTTGTCATGATC Primer 480597 (SEQ ID NO: 3):
TTTATTACGCGTATCCCCCACAACGATTTTCCTGTC PCR on B. subtilis nucB:
Primer 480598 (SEQ ID NO: 4):
TTATTTATCGATAAGGTATGGGGGGATGGGGATGAAAAAATGG Primer 480599 (SEQ ID NO: 5):
TTATTTACGCGTCAGCTCGGCGAAGGATTGTAACAAC
```

These plasmids were each transformed into *B. subtilis* and plasmid preps were made. Restriction digests of the plasmids showed major break down of DNA which indicated that both the *B. subtilis* and *B. licheniformis* nucB genes were fully induced and the encoded nucleases could both be expressed into the medium. The two strains were kept as:
  MOL2676 (B. lich. nucB) pMOL2676
  MOL2677 (B. sub. nucB) pMOL2677
Donor strains were kept as:
  MOL2680 (B. lich. nucB) pMOL2676
  MOL2681 (B. sub. nucB) pMOL2677

In a more controlled experiment, we inoculated the strains in TY, incubated at 37° C. overnight, and mixed cell free 10 microliters of supernatant with marker DNA (1 Kb ladder). The samples were incubated at 37° C. for different time intervals. There was major degradation of the marker DNA for the strain with the cloned nucB genes as compared to the control strains. The conclusion was that the nucB genes can both be expressed into functional nucleases in *B. subtilis*.

Example 5

Results on Ppst Induced nucB Expression

Figure 8:
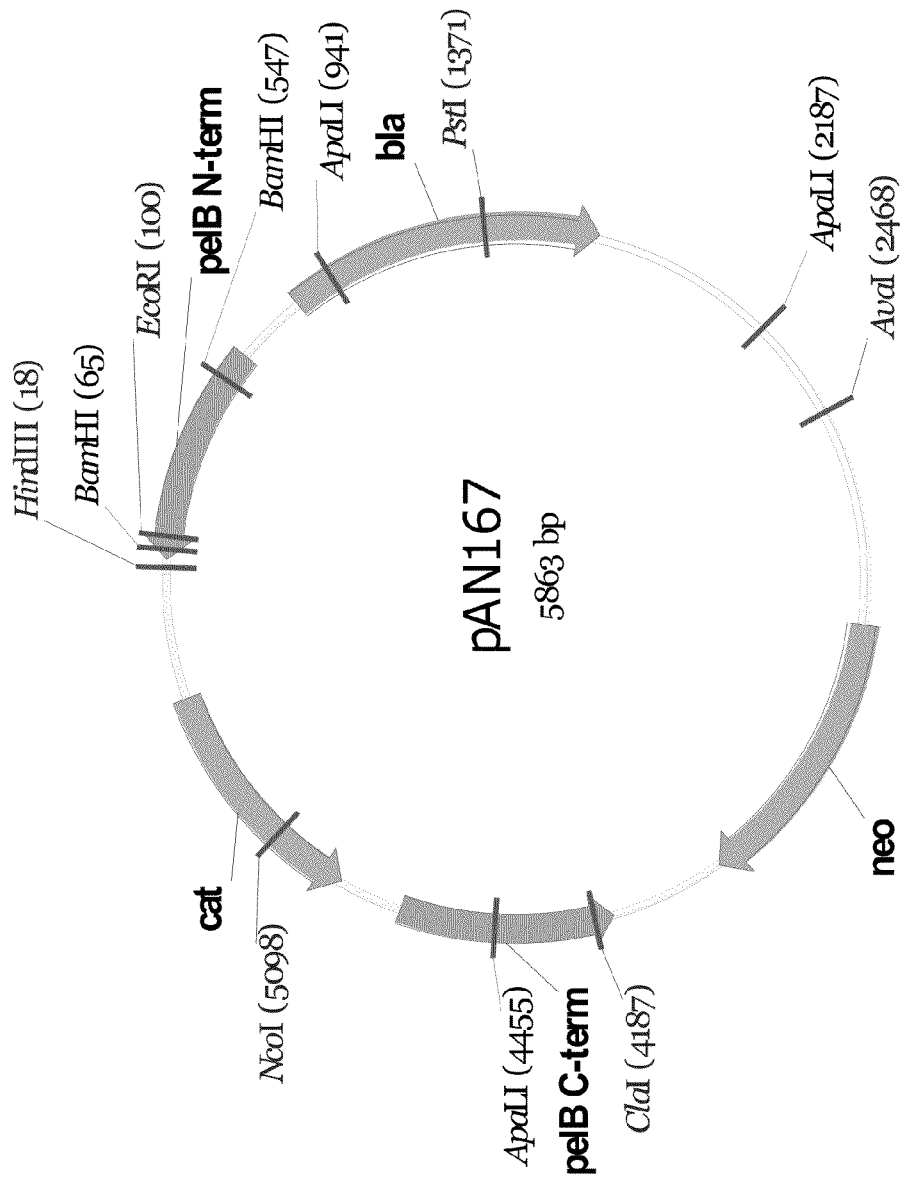
FIG. 8. A cloning vector expression system denoted pAN167, the full DNA sequence of this plasmid is shown in SEQ ID NO: 6.

The second cloning strategy was to exploit the tightly controlled pstS promoter from *B. licheniformis* to express the nuclease under phosphate limited conditions, such as towards the end of a fermentation. Again, both of the nucB genes were amplified by PCR and cloned together with the pstS promoter into another plasmid pAN167, that was designed for integration into the pel locus in the *B. subtilis* chromosome. The DNA sequence of pAN167 is provided in SEQ ID NO: 6, and the restriction map is shown in FIG. 8.

```
PCR on Ppst from strain PP2201-1-Ppst-GFP
Primer Cat, aa49, forw (SEQ ID NO: 7):
```

-continued

CCTTTATTAATGAATTTTCCTGCTG

Primer GFP, aa17, rev (SEQ ID NO: 8):
CAACAAGAATTGGGACAACTCCAGTG

PCR on B. licheniformis nucB
Primer 491264 (SEQ ID NO: 9):
TTTATTACGCGTCAAGAGGAGGTTGTTTTTGTCATGATC Primer 492902 (SEQ ID NO: 10):
TTTATTAAGCTTATCCCCCACAACGATTTTCCTGTC PCR on B. subtilis nucB
Primer 491266 (SEQ ID NO: 11):
TTATTTACGCGTAAGGTATGGGGGGATGGGGATGAAAAAATGG Primer 492903 (SEQ ID NO: 12):
TTATTTAAGCTTCAGCTCGGCGAAGGATTGTAACAAC The ligations were transformed into *B. subtilis* and plasmid preps were made. Restriction digests showed the correct cloning had taken place. The nucB expression cassette with the pst promoter was integrated in the pel locus by double cross-over recombination and correct integration was verified by PCR. The following strains were preserved:

MOL2684, MOL2685: integration of construct with nucB from *B. licheniformis*

MOL2686, MOL2687: integration of construct with nucB from *B. subtilis*

In order to study if the pst promoter was able to activate the nucB gene at low phosphate concentration, a series of samples was set up. The two strains MOL2684 and MOL2686 were innoculated in TY medium with and without added phosphate. After an overnight growth at 37° C., the cells were pelleted and the supernatant was examined for nuclease activity by mixing it with marker DNA according to FIG. 9. 10 microliters of cellfree supernatant was applied with marker DNA (1 Kb ladder). The samples were incubated at 37° C. for different time intervals.

As seen in FIG. 9 there is major degradation of the marker DNA for the strain with the cloned *B. licheniformis* nucB gene as compared to the control strains, but only in fermentations without added phosphate. In fermentations with a surplus of phospate there is no trace of degradation.

The conclusion is that the nucB gene from *B. licheniformis* can be expressed from the Ppst promoter and is tightly controlled by the level of phophate in the medium.

Example 6

Ppst Induced nucB Expression in Commercially Relevant Conditions

We wanted to test the Ppst-nucB construct in a relevant amylase production strain used for expression of food enzymes, in commercially relevant fermentation conditions. Chromosomal DNA from strain MOL2684 and MOL2685 was used to transform the production strain, selecting for chloramphenicol resistance. The presence of the nucB expression cassette was verified by PCR.

The resulting strains expressing nucB from the Ppst promoter integrated into the pel locus were preserved as: MOL2716, MOL2717, MOL2718 (integration of construct with nucB from *B. licheniformis*).

One of the resulting strains, MOL2717, was then fermented in 1 liter scale to investigate if the initiation of expression and activity of the NucB nuclease was sufficient to digest DNA. The fermentation was run as a phosphatase limited process through a four day fermentation and samples were taken each day. The samples were cleared for cells by centrifugation and mixed with marker DNA to examine the DNase activity. Results from this experiment are shown in FIG. 10. The lanes with samples from 1 litre scale fermentations show a slow degradation of DNA compared to earlier experiments, but after 240 min there is marked digestion of DNA resulting in diffuse bands. The controls show the expected activity.

The invention claimed is:

1. A *Bacillus* cell transformed with a first expression vector comprising a nucleic acid encoding at least one enzyme of interest and a second expression vector comprising a nucleic acid encoding at least one nuclease, wherein the *Bacillus* cell is able to secrete the enzyme(s) of interest and nuclease(s) into a fermentation broth resulting in reduced DNA in the fermentation broth compared to an otherwise isogenic *Bacillus* cell without the vector that encodes at least one nuclease.

2. The *Bacillus* cell of claim 1, wherein the cell is a *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, or *Bacillus thuringiensis* cell.

3. The *Bacillus* cell of claim 1, wherein the at least one enzyme of interest is a lyase, a ligase, a hydrolase, an oxidoreductase, a transferase, or an isomerase.

4. The *Bacillus* cell of claim 1, wherein the cell is a *Bacillus licheniformis* cell.

5. The *Bacillus* cell of claim 1, wherein the at least one enzyme of interest is a hydrolase.

6. The *Bacillus* cell of claim 1, wherein the at least one nuclease is transcribed from a constitutive promoter.

7. The *Bacillus* cell of claim 1, wherein the at least one nuclease is transcribed from a regulated promoter.

8. The *Bacillus* cell of claim 7, wherein the regulated promoter is upregulated in response to phosphate-limitation in the growth medium.

9. A method for producing an enzyme of interest significantly free from contaminating DNA, said method comprising the steps of: cultivating in a growth medium the *Bacillus* cell of claim 1 and separating the cells from the growth medium.

10. The method of claim 9, comprising the step of isolating the enzyme of interest from the growth medium.

11. The method of claim 9, wherein the cell is a *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, or *Bacillus thuringiensis* cell.

12. The method of claim of claim 9, wherein the at least one enzyme of interest is a lyase, a ligase, a hydrolase, an oxidoreductase, a transferase, or an isomerase.

13. The method of claim 9, wherein the one or more recombinant nuclease encoding gene(s) is integrated into the genome of said cell.

14. The method of claim 9, wherein the cell is a *B. licheniformis* cell.

15. The method in accordance with claim 9, wherein the enzyme is a lyase.

16. The method in accordance with claim 9, wherein the enzyme is a ligase.

17. The method in accordance with claim 9, wherein the enzyme is a hydrolase.

18. The method in accordance with 9, wherein the enzyme is an oxidoreductase.

19. The method in accordance with claim 9, wherein the enzyme is a transferase.

20. The method in accordance with of claim 9, wherein the enzyme is or an isomerase.

* * * * *